(12) United States Patent
Morgan et al.

(10) Patent No.: US 11,826,346 B2
(45) Date of Patent: Nov. 28, 2023

(54) METHODS OF INCREASING MAGNESIUM BIOAVAILABILITY AND ABSORPTION

(71) Applicant: Balchem Corporation, New Hampton, NY (US)

(72) Inventors: Shane Christopher Morgan, South Weber, UT (US); Ren A. Gonzalez, Nibley, UT (US)

(73) Assignee: Balchem Corporation, New Hampton, NY (US)

( * ) Notice: Subject to any disclaimer, the term of this patent is extended or adjusted under 35 U.S.C. 154(b) by 0 days.

(21) Appl. No.: 17/513,276

(22) Filed: Oct. 28, 2021

(65) Prior Publication Data

US 2022/0125759 A1  Apr. 28, 2022

Related U.S. Application Data

(60) Provisional application No. 63/106,543, filed on Oct. 28, 2020.

(51) Int. Cl.
*A61K 31/375* (2006.01)
*A61K 33/06* (2006.01)
*A61P 3/02* (2006.01)

(52) U.S. Cl.
CPC ............ *A61K 31/375* (2013.01); *A61K 33/06* (2013.01); *A61P 3/02* (2018.01)

(58) Field of Classification Search
None
See application file for complete search history.

(56) References Cited

U.S. PATENT DOCUMENTS

| 5,626,883 | A | | 5/1997 | Paul |
| 5,849,337 | A | | 12/1998 | Dixon |
| 5,849,338 | A | * | 12/1998 | Richardson ............ A61K 33/06 |
| | | | | 514/474 |
| 8,017,160 | B2 | | 9/2011 | Jaffe |
| 8,178,132 | B2 | | 5/2012 | Liu et al. |
| 2005/0244510 | A1 | | 3/2005 | Smith |
| 2005/0220865 | A1 | | 10/2005 | Koleng et al. |

FOREIGN PATENT DOCUMENTS

| IT | 201800007747 A1 | * | 2/2020 |
| WO | WO 2011003045 | * | 1/2011 |

OTHER PUBLICATIONS

International Search Report and Written Opinion for PCT/US2021/057021 dated Jan. 26, 2022, 16 pages.

* cited by examiner

*Primary Examiner* — Danah Al-Awadi
(74) *Attorney, Agent, or Firm* — POLSINELLI PC (57) ABSTRACT

The present disclosure relates to compositions and methods of increasing magnesium bioavailability and absorption.

18 Claims, 7 Drawing Sheets

METHODS OF INCREASING MAGNESIUM BIOAVAILABILITY AND ABSORPTION

CROSS-REFERENCE TO RELATED APPLICATIONS

This application claims priority to U.S. Provisional Application No. 63/106,543 entitled "METHODS OF INCREASING MAGNESIUM BIOAVAILABILITY AND ABSORPTION" filed on Oct. 28, 2020, the entirety of which is incorporated herein by reference.

FIELD OF THE DISCLOSURE

The present disclosure relates to compositions and methods of increasing magnesium bioavailability and absorption.

BACKGROUND OF THE DISCLOSURE

Magnesium is an essential mineral, and is involved in hundreds of biochemical reactions in vivo, including protein synthesis, muscle and nerve functioning, bone development, energy production, the maintenance of normal heart rhythm, and the regulation of glucose and blood pressure. Poor dietary intake of magnesium has become increasingly common. Over time, low magnesium can increase the risk of illnesses, including high blood pressure and heart disease, diabetes mellitus type 2, osteoporosis, and migraines.

Magnesium deficiency may by caused by gastrointestinal or kidney issues. Gastrointestinal causes include inadequate dietary intake of magnesium, reduced gastrointestinal absorption or increased gastrointestinal loss due to rapid gastrointestinal transit time. Kidney causes involve increased excretion of magnesium.

There is a need in the art for bioavailable magnesium compositions to aid in increasing magnesium levels in a subject.

SUMMARY OF THE DISCLOSURE

Disclosed herein is a method for increasing magnesium absorption in a subject comprising administering a magnesium source and ascorbate to the subject. The magnesium source may include a magnesium salt or a magnesium chelate. The ascorbate may be from ascorbic acid or an ascorbate salt, such as magnesium ascorbate. The magnesium source and the ascorbate may be formulated into a single composition. The magnesium source and the ascorbic acid may be administered separately, but within 15 minutes of each other. The ratio of the ascorbic acid to the magnesium may be between about 1:1 to about 5:1. The magnesium and the ascorbate may be administered orally. The method may increase absorption by at least 55%. The absorption may be via the subject's gastrointestinal tract. The subject may be a livestock animal, a human, or a non-human primate.

Further provided herein is a method for increasing magnesium absorption in a subject comprising administering a pharmaceutical composition comprising magnesium and ascorbate to the subject. The magnesium may be a magnesium salt or a magnesium chelate. The ascorbate may be from ascorbic acid or from an ascorbate salt, such as magnesium ascorbate. The ratio of the ascorbic acid to the magnesium in the pharmaceutical composition may be about 1:1 to about 5:1. The magnesium and the ascorbate may be administered orally. The pharmaceutical composition may be a solid dosage form selected from the group consisting of a tablet, a capsule, a powder, or a granule; alternatively, the pharmaceutical composition may be a liquid. The method may increase absorption by at least 55%. The absorption may occur in the subject's gastrointestinal tract. The subject may be a livestock animal, a human, or a non-human primate.

Further provided herein is a method for increasing magnesium bioavailability in a subject comprising administering a pharmaceutical composition comprising administering a pharmaceutical composition comprising magnesium and ascorbate to the subject. The magnesium may be a magnesium salt or a magnesium chelate. The ascorbate may be from ascorbic acid or an ascorbate salt, such as magnesium ascorbate. The ratio of ascorbic acid to magnesium in the pharmaceutical composition is between about 1:1 to about 5:1. The magnesium and the ascorbate may be administered orally. The pharmaceutical composition may be a solid dosage form selected from the group consisting of a tablet, a capsule, a powder, or a granule; alternatively, the pharmaceutical composition may be a liquid. The method may increase absorption by at least 55%. The absorption may be in the subject's gastrointestinal tract. The subject may be a livestock animal, a human, or a non-human primate.

Further provided herein is a method for decreasing side effects from magnesium supplementation in a subject, the method comprising administering a pharmaceutical composition comprising magnesium and ascorbate to the subject. The side effects may include one or more of stomach upset, nausea, diarrhea, and vomiting. The magnesium may be a magnesium salt or a magnesium chelate. The ascorbate may be from ascorbic acid or an ascorbate salt, such as magnesium ascorbate. The ratio of ascorbic acid to magnesium in the pharmaceutical composition is between about 1:1 to about 5:1. The magnesium and the ascorbate may be administered orally. The pharmaceutical composition may be a solid dosage form selected from the group consisting of a tablet, a capsule, a powder, or a granule; alternatively, the pharmaceutical composition may be a liquid. Absorption of the magnesium may be via the mammal's gastrointestinal tract. The subject may be a livestock animal, a human, or a non-human primate.

Further provided herein is a method of treating magnesium deficiency in a subject, the method comprising administering a magnesium source and ascorbate to the subject. The magnesium may be a magnesium salt or a magnesium chelate. The ascorbate may be from ascorbic acid or an ascorbate salt, such as magnesium ascorbate. The ratio of ascorbic acid to magnesium in the pharmaceutical composition is between about 1:1 to about 5:1. The magnesium and the ascorbate may be administered orally. The pharmaceutical composition may be a solid dosage form selected from the group consisting of a tablet, a capsule, a powder, or a granule; alternatively, the pharmaceutical composition may be a liquid. The method may increase absorption by at least 55%. The absorption may be via the subject's gastrointestinal tract. The subject may be a livestock animal, a human, or a non-human primate.

DETAILED DESCRIPTION

The present disclosure encompasses compositions and methods to increase magnesium bioavailability and absorption in a subject.

I. Compositions

Compositions of the present disclosure comprise a magnesium source and ascorbate. Each of these components are described in more detail below.

(a) Magnesium Source

A composition of the present disclosure comprises a magnesium source. Many magnesium sources are suitable, as long as the source provides bioavailable magnesium to the subject.

In certain embodiments, the magnesium source may be a magnesium salt. Such salts may be inorganic or organic salts, and the present disclosure contemplates salts with different hydration states. Non-limiting examples of such salts may include magnesium chloride, Mg sulfate, Mg bromide, Mg carbonate, Mg phosphates, etc. as inorganic salts. Mg citrate, Mg malate, or dimagnesium malate, Mg threonate, Mg taurate, Mg orotate, and other similar compounds can be targeted as organic salts.

In a particular embodiment, the magnesium salt may be magnesium ascorbate.

In other embodiments, the magnesium source may be a magnesium chelate. Non-limiting examples of such chelates may include magnesium bis-amino acid chelates, di-amino acid chelates, or tri-amino acid chelates. Specific examples of bis-amino acid chelates include magnesium bisglycinate and magnesium lysinate glycinate, although one of skill in the art will appreciate that other Mg chelates will also work.

A di-amino acid suitable for a magnesium di-amino acid chelate of the present disclosure includes di-amino acids capable of forming at least two coordinate bonds with a magnesium ion. In preferred embodiments, a di-amino acid suitable for use in the present disclosure includes di-amino acids capable of forming between 2 and 6 coordinate bonds with respect to magnesium.

In some embodiments, a di-amino acid suitable for use in the present disclosure forms chelate bonds at all Lewis acid locations within the di-amino acid. In some further embodiments, a di-amino acid suitable for use in the present disclosure does not form chelate bonds via carbonyl groups. In other embodiments, a di-amino acid suitable for use in the present disclosure does form chelate bonds via a carbonyl group.

In one embodiment, the di-amino acid is di-glycine, also called herein $G_2$, 2-[(2-Aminoacetyl)amino]acetic acid, or glycylglycine. In other non-limiting embodiments, the di-amino acid may be di-aspartic acid ($D_2$), di-glutamic acid ($E_2$), di-histidine ($H_2$), di-serine ($S_2$), or di-tyrosine ($Y_2$). In still other non-limiting embodiments, the di-amino acid may be comprised of two amino acids, each selected form the group consisting of glycine (G), aspartic acid (D), glutamic acid (E), histidine (H), serine (S), and tyrosine (Y). For instance, a di-amino acid may be GD, GE, GH, GS, GY, GG, DG, ED, DE, or other combinations.

A tri-amino acid suitable for a magnesium tri-amino acid chelate of the present disclosure includes tri-amino acids capable of forming at least two coordinate bonds with a magnesium ion. In preferred embodiments, a tri-amino acid suitable for use in the present disclosure includes tri-amino acids capable of forming between 2 and 6 coordinate bonds with respect to magnesium.

In some embodiments, a tri-amino acid suitable for use in the present disclosure forms chelate bonds at all Lewis acid locations within the tri-amino acid. In some further embodiments, a tri-amino acid suitable for use in the present disclosure does not form chelate bonds via carbonyl groups. In other embodiments, a tri-amino acid suitable for use in the present disclosure does form chelate bonds via a carbonyl group.

In one embodiment, the tri-amino acid is tri-glycine, also called herein $G_3$, 2-[[2-[(2-aminoacetyl)amino]acetyl]amino]acetic acid, or glycylglycylglycine. In other embodiments, the tri-amino acid may be tri-aspartic acid ($D_3$), tri-glutamic acid ($E_3$), tri-histidine ($H_3$), tri-serine ($S_3$), or tri-tyrosine ($Y_3$). In still other embodiments, the tri-amino acid may be comprised of three amino acids, each selected from the group consisting of glycine (G), aspartic acid (D), glutamic acid (E), histidine (H), serine (S), and tyrosine (Y). For instance, a tri-amino acid may be GDG, GGD, DGG, EDG, GDE, or other combinations.

In further embodiments, the magnesium source may be a magnesium base, such as Mg oxide or Mg hydroxide.

(b) Ascorbate

A composition of the present disclosure comprises ascorbate. The ascorbate may be derived from any ascorbate source that can be administered to a subject. In one embodiment, the ascorbate may be from ascorbic acid. In another embodiment, the ascorbate may be from an ascorbate salt. In a particular embodiment, the ascorbate may be magnesium ascorbate. In other particular embodiments, the ascorbate may be selected from the group consisting of calcium ascorbate, sodium ascorbate, and iron ascorbate.

(c) Ratio

The molar ratio of ascorbate to magnesium may vary from about 0.75:1 to about 5:1 or greater than 5:1. At molar ratios greater than 5:1, increased magnesium absorption may still be seen compared to the same magnesium source without ascorbate, but the increase in absorption is not as great as the increase seen at lower ratios. In some embodiments, the molar ratio of ascorbate to magnesium may vary from about 1:1 to about 4:1. In other embodiments, the molar ratio of ascorbate to magnesium may vary from about 1:1 to about 2:1. In still other embodiments, the molar ratio of ascorbate to magnesium may be about 0.75:1, 1:1, 1.25:1, 1.5:1, 1.75:1, 2:1, 2.25:1, 2.5:1, 2.75:1, 3:1, 3.25:1, 3.5:1, 3.75:1, 4:1, 4.25:1, 4.5:1, 4.75:1, or 5:1.

(d) Dosages

Generally speaking, a composition of the present invention may comprise at least about 25 mg to about 750 mg magnesium. In some embodiments, a composition of the present invention may comprise about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 235, 240, 245, 250, 255, 260, 265, 270, 275, 280, 285, 290, 300, 305, 310, 315, 320, 325, 330, 335, 340, 345, 350, 355, 360, 365, 370, 375, 380, 385, 390, 400, 405, 410, 415, 420, 425, 430, 435, 440, 445, 450, 455, 460, 465, 470, 475, 480, 485, 490, 500, 505, 510, 515, 520, 525, 530, 535, 540, 545, 550, 555, 560, 565, 570, 575, 580, 585, 590, 600, 605, 610, 615, 620, 625, 630, 635, 640, 645, 650, 655, 660, 665, 670, 675, 680, 685, 690, 700, 705, 710, 715, 720, 725, 730, 735, 740, 745, 750, or more than 750 mg magnesium.

In certain embodiments, a composition of the present invention may comprise about 25 to about 100, about 75 to about 200, about 175 to about 300, about 275 to about 400, about 375 to about 500, about 475 to about 600, about 575 to about 700, about 675 to about 750, or about 700 to more than 750 mg magnesium.

A composition of the present invention may be administered once daily, or may be administered more than once daily. As would be appreciated in the art, compositions formulated to be administered more than once daily may comprise less magnesium than once a day formulations.

Of note, the increased magnesium bioavailability and absorption from a composition of the present invention may mean that less magnesium is needed to achieve a particular in vivo magnesium level in a subject.

(e) Formulations

Another aspect of the present invention is a pharmaceutical formulation comprising a composition detailed above. A pharmaceutical formulation may be prepared for oral administration, or any other suitable route of administration. A pharmaceutical formulation comprises a composition as described above, as an active ingredient, and at least one pharmaceutically acceptable carrier. The term oral, as used herein, includes sub-lingual and gavage.

The pharmaceutical formulation may be formulated into various dosage forms and administered by a number of different means that will deliver a therapeutically effective amount of the active ingredient. Such compositions can be administered in dosage unit formulations containing conventional nontoxic pharmaceutically acceptable carriers, adjuvants, and vehicles as desired. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980).

Certain embodiments of the invention relate to oral formulations and oral administration. Oral formulations generally may include an inert diluent or an edible carrier. Oral formulations may be enclosed in gelatin capsules, compressed into tablets, or otherwise be formulated as a troche, a powder, a granule, a gummy, a soft gel, a soft chew, a chewable tablet, or the like. Oral compositions may also be prepared using a fluid carrier. Pharmaceutically compatible binding agents and/or adjuvant materials may be included as part of the composition.

The active components of a solid-type dosage form for oral administration can be mixed with at least one additive, such as sucrose, lactose, cellulose, mannitol, trehalose, raffinose, maltitol, dextran, starches, agar, alginates, chitins, chitosans, pectins, gum tragacanth, gum arabic, gelatin, collagen, casein, albumin, synthetic or semisynthetic polymer, or glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidants such as cysteine, disintegrators, binders, thickeners, buffering agents, pH adjusting agents, sweetening agents, flavoring agents or perfuming agents. Liquid dosage forms for oral administration may comprise the active components mixed with at least one aqueous solvent. Liquid oral compositions may further comprise preserving agents, buffering agents, pH adjusting agents, sweetening agents, flavoring agents, or the like.

A therapeutically effective dose for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by one of appropriate skill in the art.

Still another aspect of the present invention is a nutraceutical formulation comprising a composition detailed above. A nutraceutical formulation comprises a composition described above, as an active ingredient, and an edible carrier. For instance, in some embodiments, the nutraceutical may be a food or food ingredient that comprises a composition described above. Suitable edible carriers are known in the art.

(f) Preferred Embodiments

In a preferred embodiment, a composition of the invention comprises magnesium ascorbate.

In another preferred embodiment, a composition of the invention comprises magnesium bisglycinate and ascorbic acid, in a molar ratio of ascorbic acid to magnesium bisglycinate of 1:1 to 5:1, preferably from 2:1 to 4:1.

In another preferred embodiment, a composition of the invention comprises magnesium chloride and ascorbic acid, in a molar ratio of ascorbic acid to magnesium chloride of 1:1 to 5:1, preferably from 2:1 to 4:1.

In yet another preferred embodiment, a composition of the invention comprises magnesium oxide and ascorbic acid, in a molar ratio of ascorbic acid to magnesium oxide of 3:2.

In still another preferred embodiment, a composition of the invention comprises magnesium citrate and ascorbic acid, in a molar ratio of ascorbic acid to magnesium citrate of 3:2.

II. Methods

The present disclosure encompasses methods of increasing absorption and bioavailability of magnesium in a subject, methods of treating magnesium deficiency in a subject, and methods of decreasing the side effects of magnesium administration to a subject. As used herein, absorption refers to uptake of magnesium from the lumen of the GI tract. Bioavailability is used herein to refer to the amount of magnesium that enters systemic circulation after an oral dosage (i.e. the amount absorbed minus the amount lost to the first pass effect).

(a) Increasing Absorption

One embodiment of the present disclosure encompasses a method for increasing magnesium absorption in a subject. The method comprises administering a magnesium source and ascorbate to the subject. Suitable sources of magnesium are described in section I above. For instance, suitable sources of magnesium include magnesium ascorbate, magnesium bisglycinate, and magnesium chloride. Suitable sources of ascorbate are also described in section I above and include ascorbic acid or an ascorbate salt.

In certain embodiments, the magnesium source and the ascorbate source may be formulated into a single composition. In other embodiments, the magnesium source and the ascorbate source may be formulated separately and administered to the subject within about 15 min of each other. For instance, the magnesium source and the ascorbate source may be administered within about 1, 2, 3, 4, 5, 6, 7, 8, 9, 10, 11, 12, 13, 14, or 15 min of each other. In each of these embodiments, the magnesium source and the ascorbate source may be formulated into pharmaceutical compositions.

The ratio of ascorbate to magnesium is described in section I above, and typically is between 0.75:1 to 5:1, and preferably between 1:1 and 4:1, or 2:1 and 4:1. In some embodiments, the ratio may be greater than 5:1. At molar ratios greater than 5:1, increased magnesium absorption may still be seen compared to the same magnesium source without ascorbate, but the increase in absorption is not as great as the increase seen at lower ratios. In some embodiments, the molar ratio of ascorbate to magnesium may vary from about 1:1 to about 4:1. In other embodiments, the molar ratio of ascorbate to magnesium may vary from about 2:1 to about 4:1. In still other embodiments, the molar ratio of ascorbate to magnesium may be about 0.75:1, 1:1, 1.25:1, 1.5:1, 1.75:1, 2:1, 2.25:1, 2.5:1, 2.75:1, 3:1, 3.25:1, 3.5:1, 3.75:1, 4:1, 4.25:1, 4.5:1, 4.75:1, or 5:1.

A method as described herein may be used to increase absorption of magnesium in the GI tract of a subject at least 55, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700 or greater than 700% when compared to the magnesium source alone. In some embodiments, absorption of magnesium in the GI tract of a subject may increase at least 200%-600%, 200%-400%, 300%-500%, or 400%-600% with a method described herein.

Typically, the magnesium source and the ascorbate are administered to the subject orally, although any other known means of administration may be used as well. Formulations are described in section I above.

(b) Increasing Bioavailability

The present disclosure also encompasses methods for increasing magnesium bioavailability in a subject. The method comprises administering a magnesium source and ascorbate to the subject. Suitable sources of magnesium are described in section I above. For instance, suitable sources of magnesium include magnesium ascorbate, magnesium bisglycinate, and magnesium chloride. Suitable sources of ascorbate are also described in section I above and include ascorbic acid or an ascorbate salt.

In certain embodiments, the magnesium source and the ascorbate source may be formulated into a single composition. In other embodiments, the magnesium source and the ascorbate source may be formulated separately and administered to the subject within about 15 min of each other. For instance, the magnesium source and the ascorbate source may be administered within about 1, 2, 3, 4, 5, 6, 7, 8, 9, 10, 11, 12, 13, 14, or 15 min of each other. In each of these embodiments, the magnesium source and the ascorbate source may be formulated into pharmaceutical compositions.

The ratio of ascorbate to magnesium is described in section I above, and typically is between 0.75:1 to 5:1, and preferably between 1:1 and 4:1, or 2:1 and 4:1. In some embodiments, the ratio may be greater than 5:1. At molar ratios greater than 5:1, increased magnesium absorption may still be seen compared to the same magnesium source without ascorbate, but the increase in absorption is not as great as the increase seen at lower ratios. In some embodiments, the molar ratio of ascorbate to magnesium may vary from about 1:1 to about 4:1. In other embodiments, the molar ratio of ascorbate to magnesium may vary from about 2:1 to about 4:1. In still other embodiments, the molar ratio of ascorbate to magnesium may be about 0.75:1, 1:1, 1.25:1, 1.5:1, 1.75:1, 2:1, 2.25:1, 2.5:1, 2.75:1, 3:1, 3.25:1, 3.5:1, 3.75:1, 4:1, 4.25:1, 4.5:1, 4.75:1, or 5:1.

A method as described herein may be used to increase bioavailability of magnesium in the GI tract of a subject at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, or greater than 300% when compared to the magnesium source alone.

Typically, the magnesium source and the ascorbate are administered to the subject orally, although any other known means of administration may be used as well. Formulations are described in section I above.

(c) Decreasing Side Effects

One embodiment of the present disclosure encompasses a method for decreasing GI side effects from administering magnesium to a subject. The method comprises administering a magnesium source and ascorbate to the subject. Because the methods of the present disclosure result in increased absorption and bioavailability of magnesium, less magnesium needs to be administered to the subject to achieve the desired magnesium levels in the subject. Suitable sources of magnesium are described in section I above. For instance, suitable sources of magnesium include magnesium ascorbate, magnesium bisglycinate, and magnesium chloride. Suitable sources of ascorbate are also described in section I above and include ascorbic acid or an ascorbate salt.

In certain embodiments, the magnesium source and the ascorbate source may be formulated into a single composition. In other embodiments, the magnesium source and the ascorbate source may be formulated separately and administered to the subject within about 15 min of each other. For instance, the magnesium source and the ascorbate source may be administered within about 1, 2, 3, 4, 5, 6, 7, 8, 9, 10, 11, 12, 13, 14, or 15 min of each other. In each of these embodiments, the magnesium source and the ascorbate source may be formulated into pharmaceutical compositions.

The ratio of ascorbate to magnesium is described in section I above, and typically is between 0.75:1 to 5:1, and preferably between 1:1 and 4:1, or 2:1 and 4:1. In some embodiments, the ratio may be greater than 5:1. At molar ratios greater than 5:1, increased magnesium absorption may still be seen compared to the same magnesium source without ascorbate, but the increase in absorption is not as great as the increase seen at lower ratios. In some embodiments, the molar ratio of ascorbate to magnesium may vary from about 1:1 to about 4:1. In other embodiments, the molar ratio of ascorbate to magnesium may vary from about 2:1 to about 4:1. In still other embodiments, the molar ratio of ascorbate to magnesium may be about 0.75:1, 1:1, 1.25:1, 1.5:1, 1.75:1, 2:1, 2.25:1, 2.5:1, 2.75:1, 3:1, 3.25:1, 3.5:1, 3.75:1, 4:1, 4.25:1, 4.5:1, 4.75:1, or 5:1.

A method as described herein may be used to decrease GI side effects known to be associated with magnesium supplementation. For instance, a method described herein may reduce stomach upset, nausea, vomiting, or diarrhea.

Typically, the magnesium source and the ascorbate are administered to the subject orally, although any other known means of administration may be used as well. Formulations are described in section I above.

(d) Treating Magnesium Deficiency

The present disclosure also encompasses methods of treating magnesium deficiency in a subject. The method comprises administering a magnesium source and ascorbate to the subject. Suitable sources of magnesium are described in section I above. For instance, suitable sources of magnesium include magnesium ascorbate, magnesium bisglycinate, and magnesium chloride. Suitable sources of ascorbate are also described in section I above and include ascorbic acid or an ascorbate salt.

In certain embodiments, the magnesium source and the ascorbate source may be formulated into a single composition. In other embodiments, the magnesium source and the ascorbate source may be formulated separately and administered to the subject within about 15 min of each other. For instance, the magnesium source and the ascorbate source may be administered within about 1, 2, 3, 4, 5, 6, 7, 8, 9, 10, 11, 12, 13, 14, or 15 min of each other. In each of these embodiments, the magnesium source and the ascorbate source may be formulated into pharmaceutical compositions.

The ratio of ascorbate to magnesium is described in section I above, and typically is between 0.75:1 to 5:1, and preferably between 1:1 and 4:1, or 2:1 and 4:1. In some embodiments, the ratio may be greater than 5:1. At molar ratios greater than 5:1, increased magnesium absorption may still be seen compared to the same magnesium source without ascorbate, but the increase in absorption is not as great as the increase seen at lower ratios. In some embodiments, the molar ratio of ascorbate to magnesium may vary from about 1:1 to about 4:1. In other embodiments, the molar ratio of ascorbate to magnesium may vary from about 2:1 to about 4:1. In still other embodiments, the molar ratio of ascorbate to magnesium may be about 0.75:1, 1:1, 1.25:1, 1.5:1, 1.75:1, 2:1, 2.25:1, 2.5:1, 2.75:1, 3:1, 3.25:1, 3.5:1, 3.75:1, 4:1, 4.25:1, 4.5:1, 4.75:1, or 5:1.

Typically, the magnesium source and the ascorbate are administered to the subject orally, although any other known means of administration may be used as well. Formulations are described in section I above.

(e) Effective Dose

As described in section I above, a therapeutically effective dose level for any particular subject will depend upon a variety of factors including the specific composition employed; the age, body weight, general health, sex and diet of the subject; the time of administration; the route of administration; the rate of excretion of the composition employed; the duration of the treatment; drugs used in combination or coincidental with the specific composition employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by one of appropriate skill in the art.

Methods of the present disclosure encompasses administration of a composition described herein as a single event or over a time course of treatment. For example, a composition can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

(f) Suitable Subjects

Methods of the present invention are suitable for any subject capable of absorbing magnesium via a gastrointestinal tract. In preferred embodiments, the subject is a vertebrate, such as a mammal or a bird. For instance, suitable subjects may include a rodent, a human, a livestock animal, a companion animal, or a zoological animal. In one embodiment, a subject may be a rodent, e.g., a mouse, a rat, a guinea pig, etc. In another embodiment, a subject may be a livestock animal. Non-limiting examples of suitable livestock animals may include chickens, turkeys, pigs, cows, horses, goats, sheep, llamas and alpacas. In still another embodiment, a subject may be a companion animal. Non-limiting examples of companion animals may include pets such as dogs, cats, rabbits, and birds. In yet another embodiment, a subject may be a zoological animal. As used herein, a "zoological animal" refers to an animal that may be found in a zoo. Such animals may include non-human primates, large cats, wolves, and bears. In certain embodiments, a subject may be human. In particular embodiments, a subject may be deficient in magnesium.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 1A:
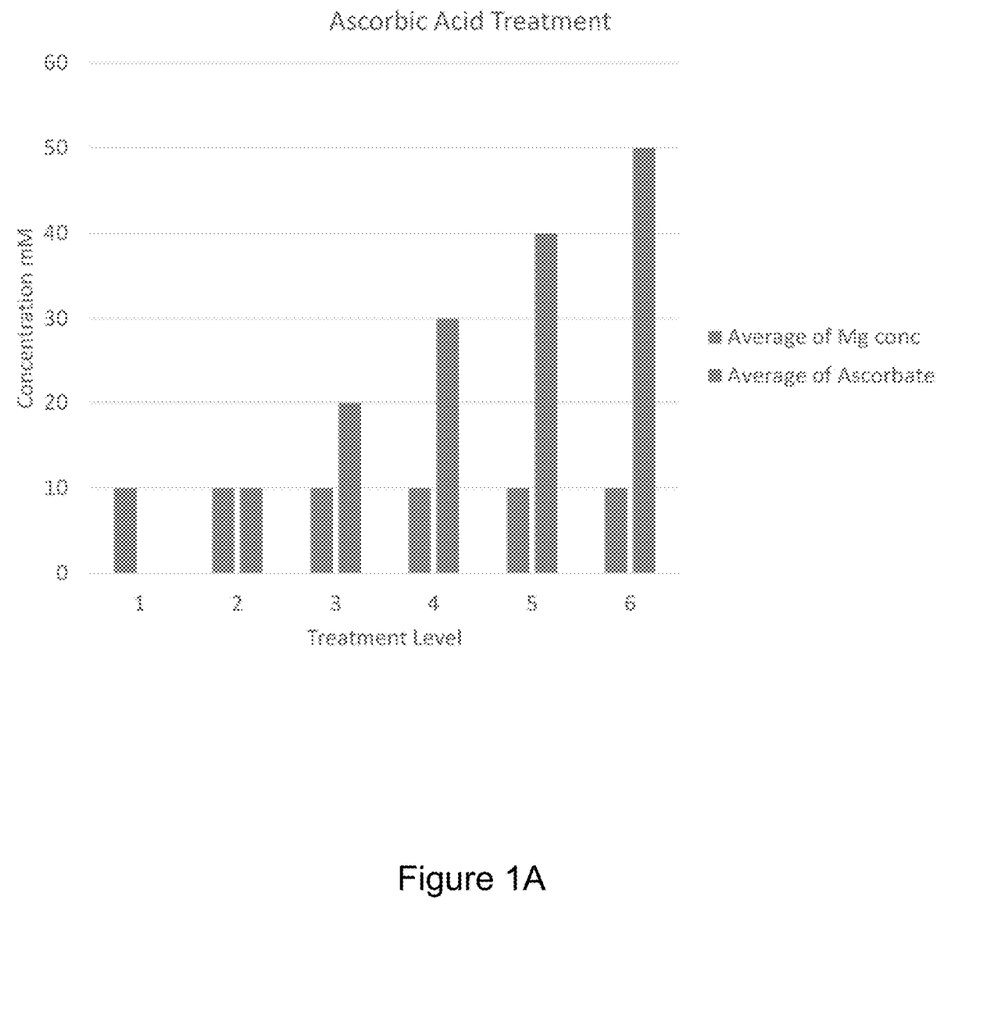
FIGS. 1A, 1B, and 1C depict graphs illustrating the six different treatment solutions used in Caco-2 in vitro transport assays (FIG. 1A), increasing magnesium absorption with increasing ascorbic acid concentration in an in vitro Caco-2 transport assay (FIG. 1B), and the reproducibility of the effect in two different experimental iterations (FIG. 1C).
Figure 1B:
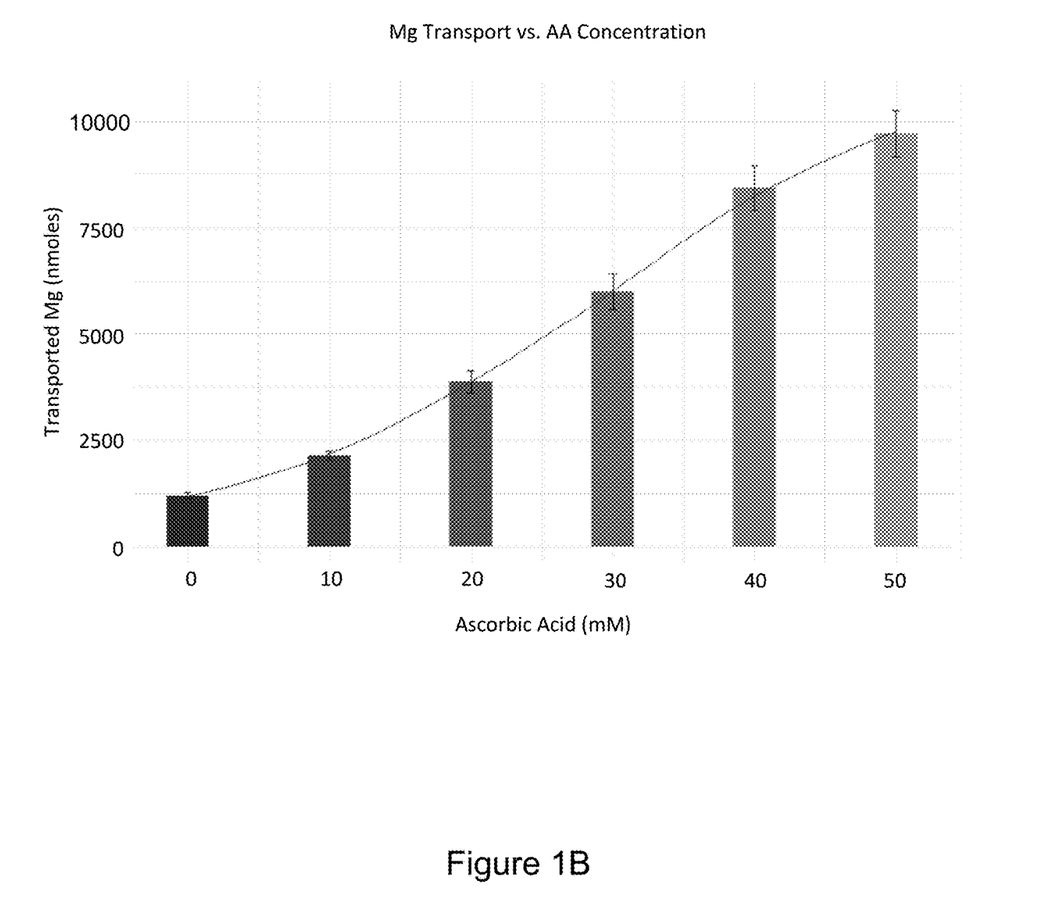

Caco-2 cells were used to model in vitro magnesium absorption of intestinal cells. The increase in magnesium absorption is dependent on the ratio of ascorbic acid to magnesium. Six different solutions, with magnesium and varying ratios of ascorbate were tested. Each solution comprised 20 mM of magnesium. Ascorbic acid ranged from 0 to 50 mM, as shown in FIG. 1A. Cells were exposed to one of the six solutions for 4 hours, then the basal media was analyzed for magnesium, using a colorimetric test. Magnesium transport increased with ascorbic acid concentration, as shown in FIG. 1B. The highest rate of magnesium transport was seen between 20 and 30 mM of ascorbic acid. Of note, the pattern is non-linear.

Figure 1C:
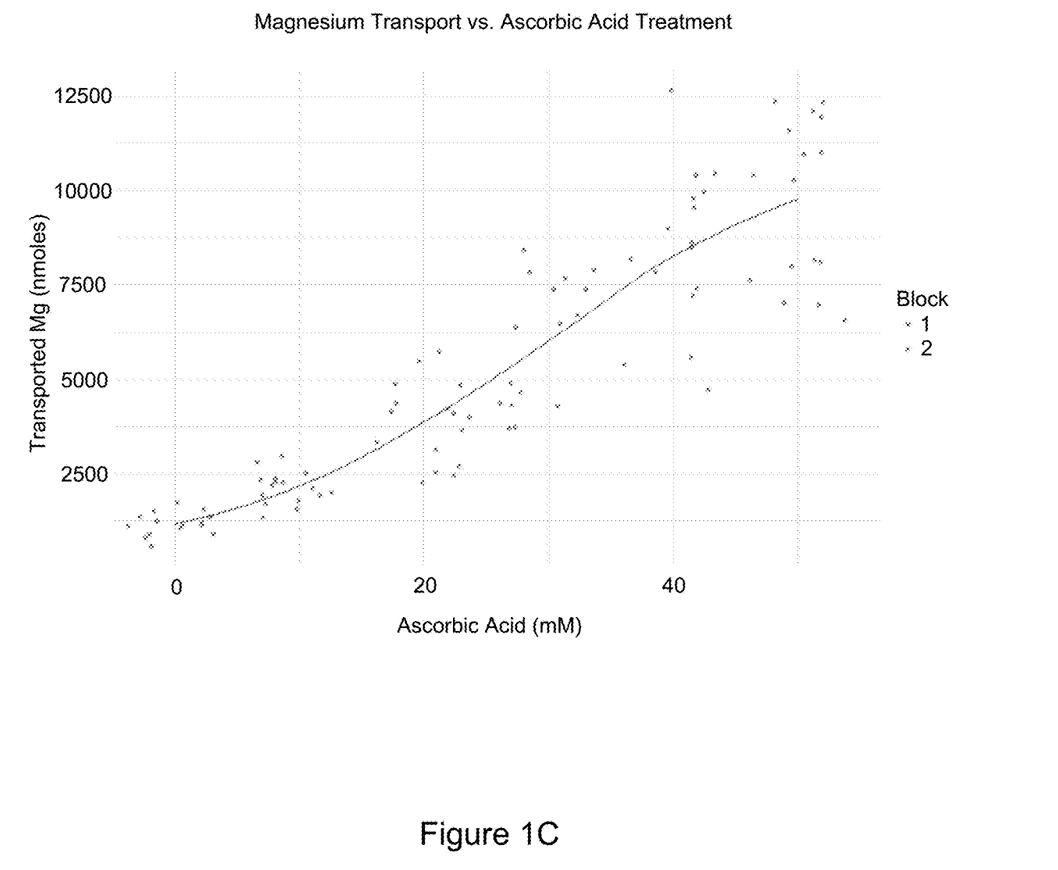

The experiment has been performed in two iterations, with the same trend apparent in each iteration (see FIG. 1C).

Example 2

Figure 2:
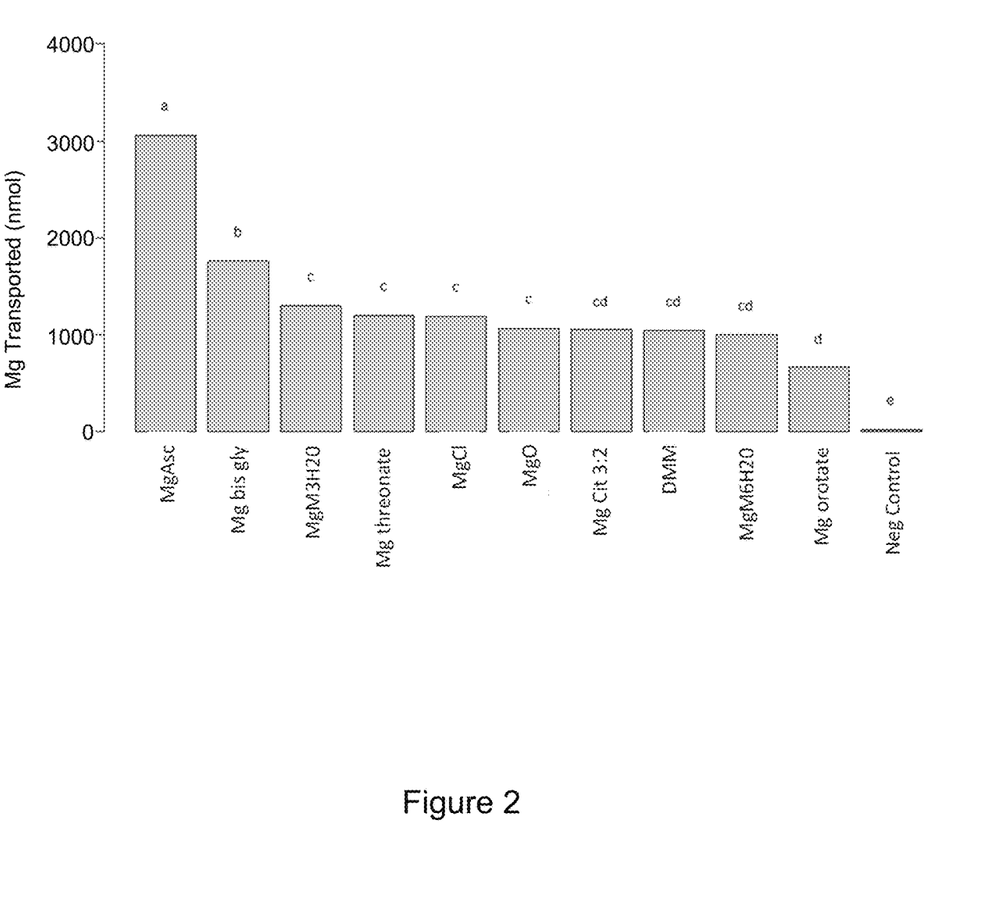
FIG. 2 depicts a graph showing magnesium transport measured in an in vitro Caco-2 model for several different treatments.

Various magnesium solutions were tested to determine their impact on magnesium transport: magnesium ascorbate, magnesium bisglycinate, magnesium orotate, magnesium threonate, and magnesium malate (trihydrate and hexahydrate; abbreviated MgM3H20 or MgM6H20 respectively in FIG. 2). Magnesium ascorbate resulted in a statistically significant higher transport rate than any other magnesium solution tested. (see FIG. 2)

Example 3

Figure 5:
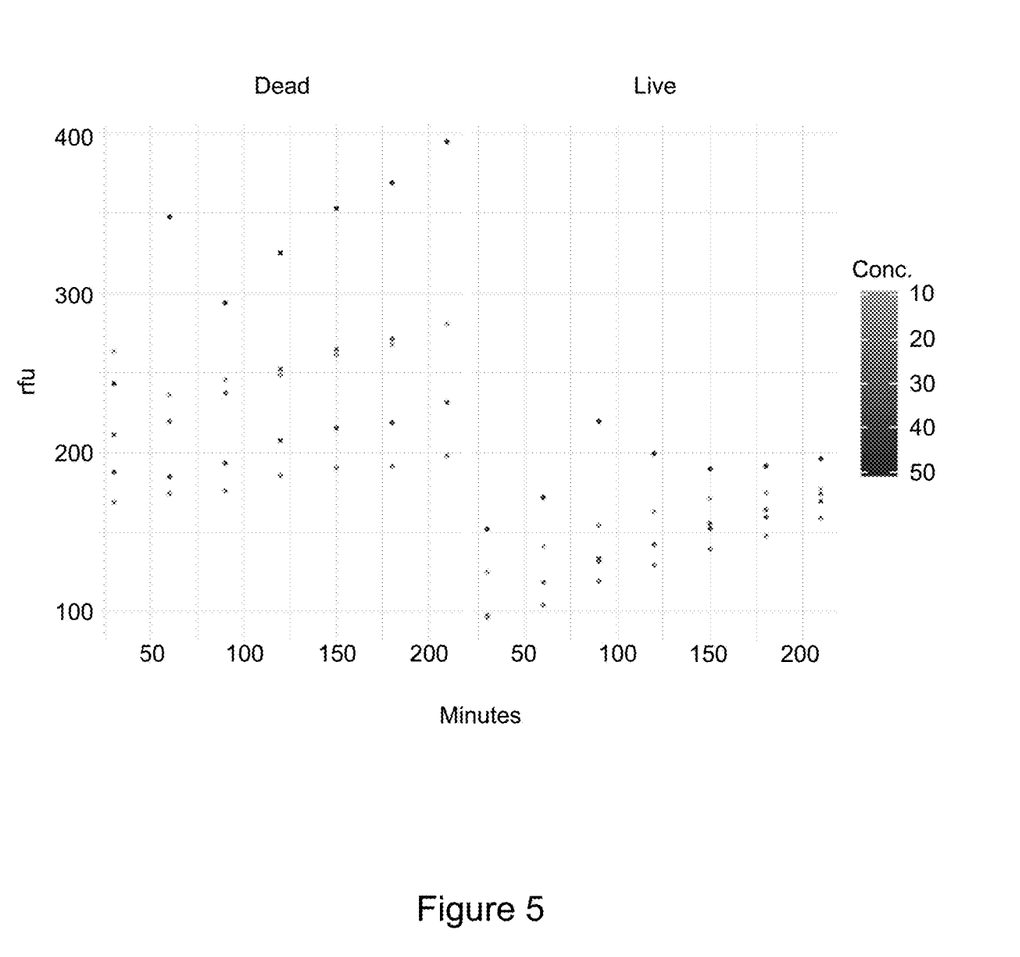
FIG. 5 depicts a graph illustrating the viability over time of cells incubated with various solutions. Caco-2 cells were propagated in T-75 tissue culture flasks for 14 days. The cells were then incubated with either 0, 5, 25, or 50 mM ascorbic acid for 240 min. Fluorescent probes were used to determine viability.

Experiments were performed to test the impact of various ascorbic acid concentrations on cell viability. Caco-2 cells were propagated in T-75 tissue culture flasks for 14 days. The cells were then incubated with either 0, 5, 25, or 50 mM ascorbic acid for 240 min. Fluorescent probes were used to determine viability. Data show no conclusive evidence that ascorbic acid kills the cells. See FIG. 5.

Example 4

Figure 3:
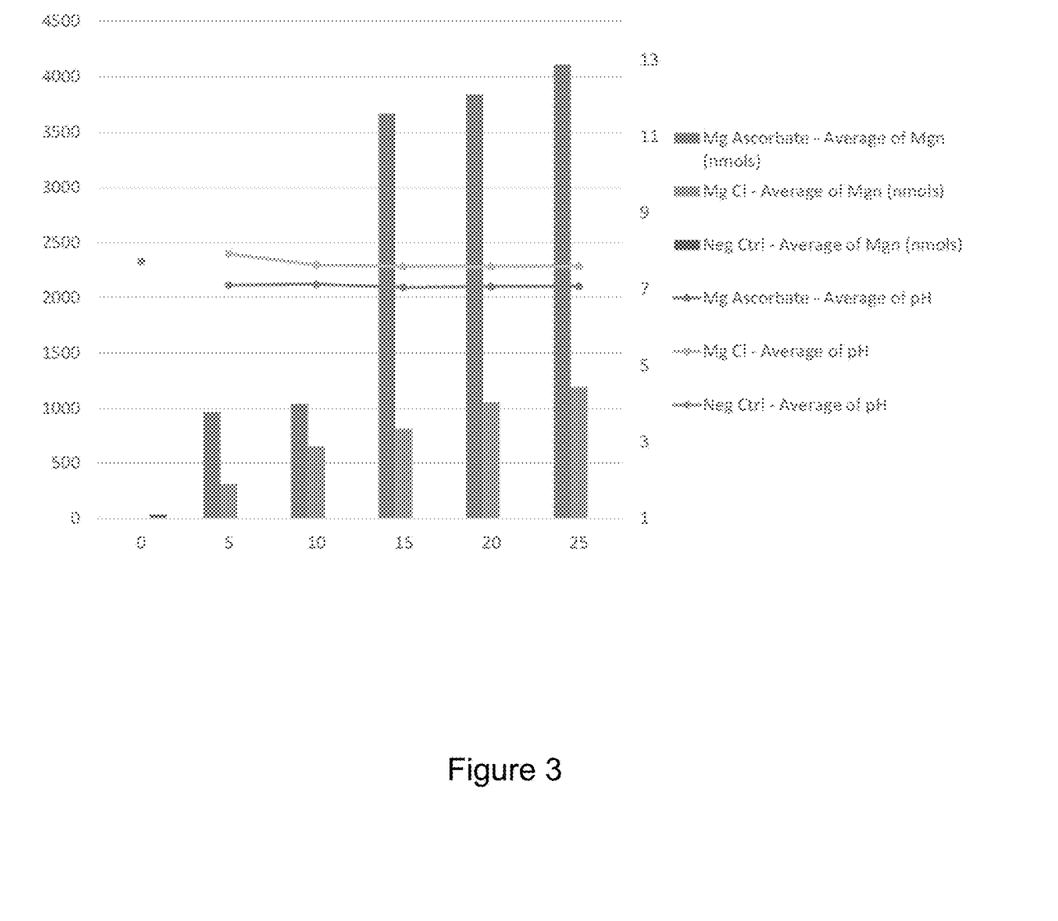
FIG. 3 depicts a graph illustrating that the increase in magnesium transport seen with magnesium ascorbate is greater than equivalent concentrations of magnesium chloride in a Caco-2 (HTB-37) in vitro model.
Figure 4:
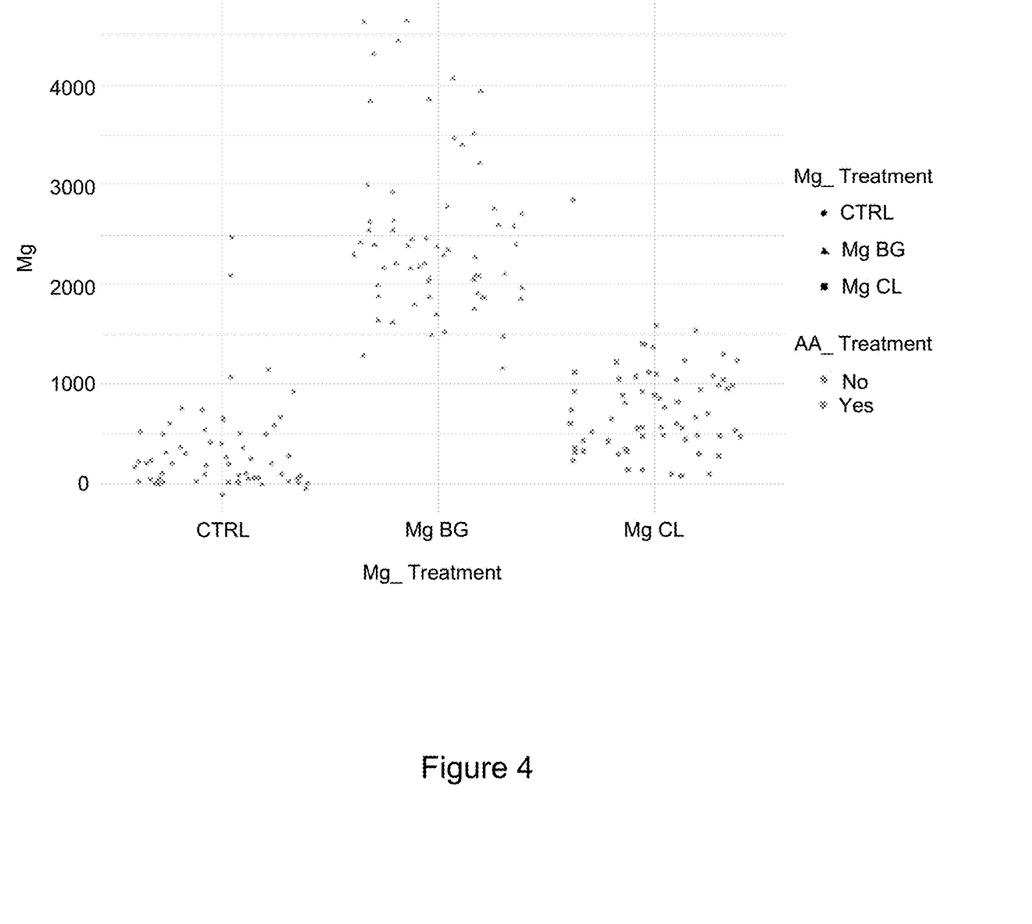
FIG. 4 depicts a graph showing Mg absorption of different Mg treatments.

Magnesium transport shows a much greater increase when magnesium ascorbate is used rather than magnesium chloride. Six different treatment concentrations were tested: 0, 5, 10, 15, 20, and 25 mg Mg (ascorbate or chloride). Increasing concentrations of magnesium chloride resulted in increased magnesium transport, in a linear fashion. Increasing concentration of magnesium ascorbate, however, resulted in a significant jump in magnesium transport between the 10 mM treatment and the 15 mM treatment. In addition, for any given concentration tested, magnesium ascorbate resulted in greater magnesium transport than magnesium chloride. (see FIG. 3) This result was not due to a change in pH resulting from an increase in ascorbic acid concentration.

What is claimed is:

1. A method for increasing magnesium absorption in a subject, the method comprising administering a magnesium source and an ascorbate source to the subject, wherein the molar ratio of the ascorbate source to the magnesium source is from about 2:1 to about 5:1, and wherein the absorption of magnesium is increased in the subject as compared to administration of the magnesium source alone.

2. The method of claim 1, wherein the magnesium source is a magnesium salt.

3. The method of claim 1, wherein the magnesium source is a magnesium chelate.

4. The method of claim 1, wherein the ascorbate source comprises ascorbic acid.

5. The method of claim 1, wherein the ascorbate source comprises an ascorbate salt.

6. The method of claim 1, wherein the ascorbate source comprises magnesium ascorbate.

7. The method of claim 1, wherein the magnesium source and the ascorbate source are formulated into a single composition.

8. The method of claim 1, wherein the magnesium source and the ascorbate source are administered separately, but within 15 min of each other.

9. The method of claim 1, wherein absorption is via the subject's GI tract.

10. The method of claim 1, wherein the magnesium source and the ascorbate source are administered orally.

11. The method of claim 1, wherein the subject is selected from the group consisting of a livestock animal, a human, or a non-human primate.

12. A method of treating magnesium deficiency in a subject, the method comprising administering a pharmaceutical composition comprising a magnesium source and an ascorbate source to the subject, wherein the molar ratio of the ascorbate source to the magnesium source in the pharmaceutical composition is from about 2:1 to about 5:1.

13. The method of claim 12, wherein the absorption is increased at least 55%.

14. The method of claim 12, wherein the pharmaceutical composition is administered orally.

15. The method of claim 12, wherein the subject is selected from the group consisting of a livestock animal, a human, or a non-human primate.

16. The method of claim 12, wherein the pharmaceutical composition is a solid dosage form selected from the group consisting of a tablet, a capsule, a powder, or a granule.

17. The method of claim 12, wherein the pharmaceutical composition is a liquid.

18. The method of claim 1, wherein the molar ratio of the ascorbate source to the magnesium source is from about 2:1 to about 4:1.

* * * * *